United States Patent [19]
Brisson et al.

[11] Patent Number: 5,203,334
[45] Date of Patent: Apr. 20, 1993

[54] TRANSDUCER MOUNTING IN LITHOTRIPTER

[75] Inventors: A. Glen Brisson, Kildeer; Exequiel D. Cruz, Arlington Heights; Dianne L. Vickers, Cary, all of Ill.

[73] Assignee: B&L Technologies, Inc., Cary, Ill.

[21] Appl. No.: 856,374

[22] Filed: Mar. 23, 1992

[51] Int. Cl.[5] .......................... A61B 8/00; A61B 17/22
[52] U.S. Cl. ............................. 128/660.03; 128/24 EL
[58] Field of Search ......................... 128/660.03, 24 EL

[56] References Cited

U.S. PATENT DOCUMENTS

| | | | |
|---|---|---|---|
| 4,986,275 | 1/1991 | Ishida et al. | 128/660.03 |
| 5,031,626 | 7/1991 | Hassler et al. | 128/24 EL |
| 5,058,569 | 10/1991 | Hassler et al. | 128/24 EL |

FOREIGN PATENT DOCUMENTS 8809253 12/1989 Fed. Rep. of Germany .

Primary Examiner—Ruth S. Smith
Assistant Examiner—Brian L. Casler
Attorney, Agent, or Firm—Robert M. Wolters

[57] ABSTRACT

A lithotripter reflector is disclosed which has an ultrasound transducer mounted at the open end of the reflector and on the axis of rotation. The transducer is supported in a brass socket, and a pair of oppositely directed arms are aligned with one another and extend in opposite directions from the housing. The outer ends of the arms are provided with steel blocks which are ground to precision size. The blocks are received in carefully milled sockets in said reflector so that insertion of the blocks in the sockets accurately positions the housing and hence the transducer.

12 Claims, 1 Drawing Sheet

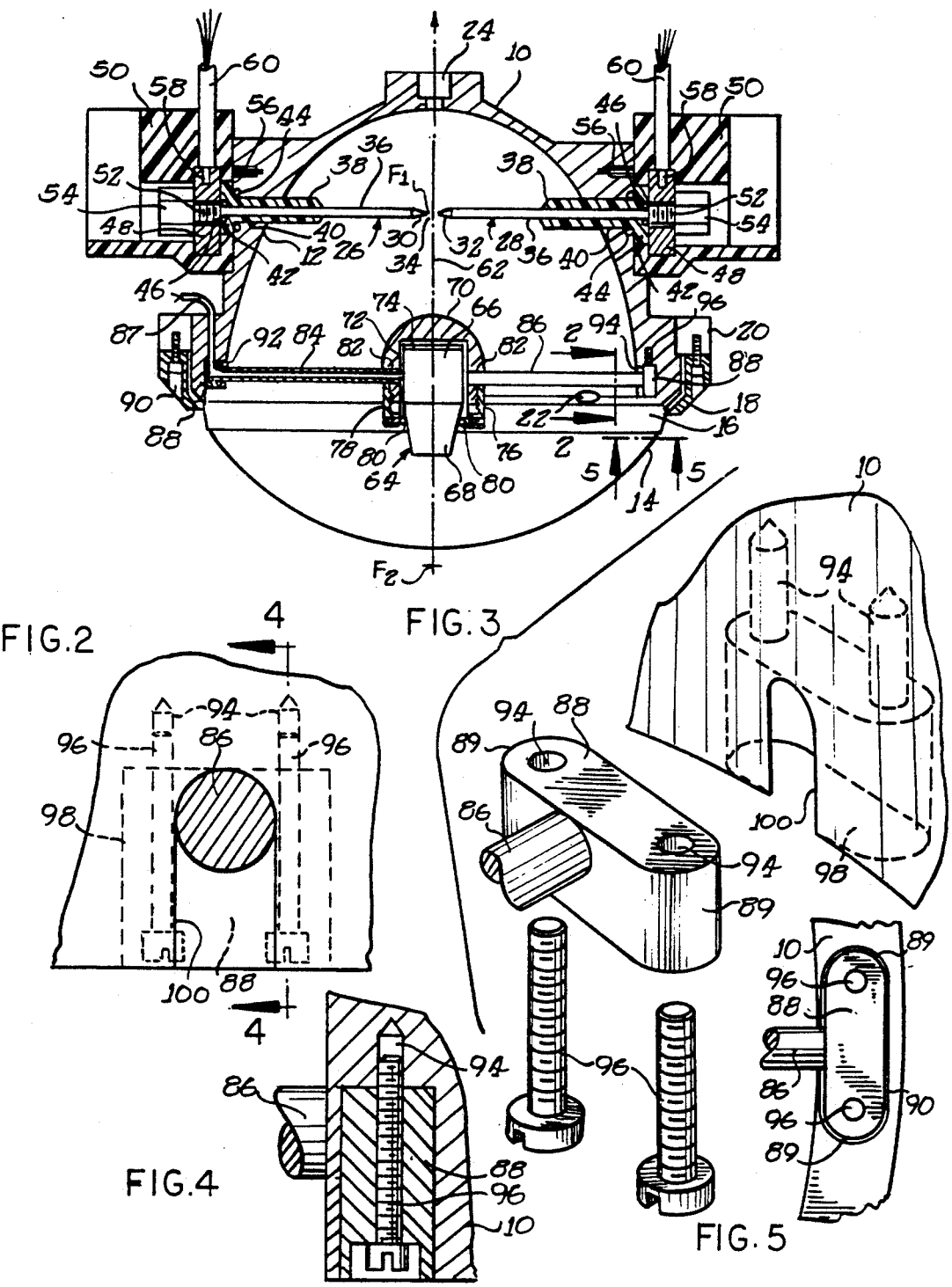

TRANSDUCER MOUNTING IN LITHOTRIPTER

BACKGROUND OF THE INVENTION

Extracorporeal lithotripters for the disintegration of kidney stones and the like without bodily invasion are well known in the art. Such lithotripters typically comprise a truncated ellipsoidal reflector. Either the entire apparatus is under water, as is a pertinent part of the patient, or a rubber diaphragm seals the otherwise open end of the lithotripter reflector. The reflector is filled with water. A pair of electrodes are spaced apart precisely at the first focal point of the reflector with the second focal point exterior the reflector beyond the diaphragm and designed to be placed on the kidney stone or other bodily concretion that is to be disintegrated. A high voltage spark across the gap between the electrode tips generates a shock wave which is focused by the walls of the reflector on the remote or second focus point. The shock wave energy so focused on the kidney stone or the like in due course reduces it to small fragments which readily pass from the body with the urine.

In many lithotripters external stone-locating devices are used, such as X-rays, or ultrasound. The detecting apparatus is often connected through a computer to positioning apparatus for the lithotripter reflector, and the reflector is mechanically brought in to proper position to place the second focus point on the kidney stone or other bodily concretion. The use of computers and mechanical controls renders the total cost of the lithotripter quite high, and beyond the purchasing power of some hospitals and clinics that would like to have one.

It is known that the reflector can be aimed by means of an ultrasound device in which an ultrasound transducer is disposed within the reflector for aiming of the reflector without the usual mechanical connections and computer, see for example U.S. Pat. No. 4,620,545 by Shene, Nowacki and Brisson. The ultrasound transducer presents a problem of mounting, in that it must be precisely aimed in the same direction as the focus of the reflector, and in that it is necessarily exposed to the shockwaves, and therefore subject to damage thereby.

OBJECTS AND SHORT SUMMARY OF THE PRESENT INVENTION

It is an object of the present invention to provide a superior mounting for an ultrasound transducer disposed within the ellipsoidal reflector of a lithotripter.

Furthermore, it is an object of the present invention to provide mounting for such a transducer which is quickly and inexpensively effected with precise positioning of the transducer.

In accordance with the present invention the ultrasound transducer is mounted within a heavy metallic housing which substantially protects it from shockwaves within the reflector. The housing is disposed at the forward edge or open end of the truncated reflector, and the transducer extends beyond the housing. The housing is supported by stainless steel arms extending to the surface of the reflector, and having stainless steel blocks on the outer ends thereof that are precision ground and are received within precision formed sockets in the wall of the transducer for precise mounting of the housing, and hence of the transducer.

THE DRAWINGS

The present invention will best be understood from the following description when taken in accompaniment with the drawings referred to wherein:

FIG. 1 is a longitudinal sectional view through the reflector and associated parts of an extracorporeal lithotripter;

FIG. 2 is a fragmentary view on an enlarged scale taken substantially along the line 2—2 in FIG. 1;

FIG. 3 is a perspective view of the precision mounting block and cooperating socket for the lithotripter housing;

FIG. 4 is a sectional view along line 4—4 in FIG. 2; and

FIG. 5 is a view looking up along line 5—5 in FIG. 1 showing one block in its socket.

DETAILED DESCRIPTION OF THE ILLUSTRATED EMBODIMENT

Referring first to FIG. 1, a lithotripter reflector assembly 10 has an ellipsoidal reflector surface 12. The reflector is aimed downwardly, and has an open lower end closed by a rubber diaphragm 14 gripped against a ring 16 at the open end of the reflector by gripping structure 18 secured to a ring 20 encircling the reflector and forming a part of the assembly. The reflector has a first focus point $F_1$ within the reflector and relatively toward the top thereof. There is a second focus point $F_2$ which is disposed beyond the diaphragm 14 and is intended for superposition on a kidney stone or the like within the body of a patient. An opening 22 provides for entrance of water, and an opening 24 at the apex of the reflector provides for the exit of water. The plumbing connections are not pertinent to the present invention and are not further shown.

A pair of electrodes 26 and 28 extend into the reflector in alignment with one another. The electrodes have spaced, tapered metallic tips 30 and 32, respectively, providing between them a gap 34 coincident with the first focus point $F_1$. A high voltage spark across the gap cause some of the water in the reflector to be flashed into steam and sets up a shock wave that is reflected by the walls of the reflecting surface or reflector 12. The electrodes 26 and 28 are mainly made of brass, and each is covered by an insulating silicone rubber sleeve 36. Each sleeve in turn is held within a plastic bushing 38 received in a respective bore 40 in the reflector assembly. Each bushing 38 has a head or flange 42 which extends radially outwardly from the axis of the respective bushing 38. An O-ring 44 is disposed beneath each flange or head 42 within a circular recess in the outer surface of the reflector housing. There is also an O-ring 46 recessed into each head and encircling the respective electrode.

A brass nut member or connector 48 is cast within each of a pair of plastic mounting members 50 made of an epoxy casting material. Each such nut member has a threaded bore through which a thicker, threaded portion 52 of the respective electrode is threaded. A hexagonal head member 54 on each electrode outer end is grippable by a wrench for threading an electrode into or out of position. Each mounting cast plastic member 50 is secured at 56 to the reflector housing. The stripped ends 58 of a pair of connecting wires 60 are secured within the brass nut members 48, and lead to spark generating apparatus, as is known in the art.

The reflector surface 12 has an axis of rotation 62, and both focus points $F_1$ and $F_2$ are on this axis. Also disposed on this axis and aimed toward the second focus point $F_2$ is an ultrasound transducer 64. The actual transducer is disposed within a plastic housing 66 which is cylindrical in its upper part. The housing further has a frustoconical tapered nose 68. As will be apparent, the housing is cylindrical about the axis of rotation 62.

The transducer 64 is mounted within a heavy brass housing 70 having a domed upper part, and cylindrical sides. A cylindrical bore 72 extends up into the housing from the lower end thereof, and the ultrasound housing at the upper bend butts against a plastic spacer disk 74. The side walls of the cylindrical portion 66 and the upper part of the tapered nose 68 are spaced from the walls of the bore 72. A retaining ring 76 is threaded on the lower end of the brass housing 70, and through a positioning ring 78 carrying an O-ring 80 is adjusted by means of three equally accurately spaced set screws 80 for final precision alignment of the transducer housing to aim the transducer specifically at the focus point $F_2$.

The brass housing 70 is provided with aligned opposite lateral or radial bores 82, and mounting arms 84 and 86 extend dimetrically therefrom. It will be noted that the arms 84 and 86 are shown in FIG. 1 as lying in the same plane as electrodes 36. Actually, the arms are at right angles to the electrodes, and are shown in the common plane for ease of illustration. The left arm 84 is hollow and carries electric wiring 87 extending to the ultrasound transducer. The right arm 86 may be either hollow or solid. Both arms are made of stainless steel, and are brazed to the brass housing 70.

A stainless steel block 88 is brazed to the outer end of each of the arms 84 and 86. The left block 88 is provided with a passageway 90 to accommodate the wire 87 leading to the transducer. An O-ring 92 encircles the arm 84 adjacent the block 88 to prevent water from leaking from the reflector to the wiring. Each block 88 has semi-cylindrical ends 89 and is machined and ground to precise specifications for precise location of the transducer 64. Each housing 88 is provided with a pair of vertical bores 94 through which extend screws 96 to secure the block in position. The two blocks, the two arms, and the transducer housing are all brazed to one another in a fixture which assures proper relative positioning of the parts.

Each block 88 is received in a complementary recess 98 which extends radially into the reflector assembly 10 and opens through the reflector surface 12 at 100 to pair the respective arms 84, 86. The recesses 98 are very carefully milled, and may be ground as necessary to be complementary to the blocks 88, to ensure precise dimensioning so that the blocks will be precisely received in the recesses and therefore will accurately position the reflector 70, through the respective arms 84 and 86. Thus, only slight correction of the positioning of the transducer 64 is necessary by way of the screws 80.

As will be apparent, the portion of the shockwave generated at the first focus point $F_1$ will directly engage the housing 70, and will also engage it indirectly by reflection from the ellipsoidal surface 12. The brass housing is relatively massive, and generally will protect the transducer 64 from the shockwaves. As will be seen, the nose 68 of the transducer extends beyond the housing, but is adequately shadowed by the housing so that reflected shockwaves will not engage it in any significant amount. Thus, the transducer is well shielded from the shockwaves. However, with the shockwave environment around the transducer, it may eventually be damaged, but it is very quickly replaced by removal of the mounting screws to remove the blocks from the recesses in which they are received. Another transducer assembly then is installed by reversal of the process.

The specific example of the invention as herein shown and described is for illustrative purposes only. Various changes in structure will no doubt occur to those skilled in the art, and will be understood as forming a part of the present invention in so far as they fall within the spirit and scope of the appended claims.

The invention is claimed as follows:

1. In an extracorporeal lithotripter comprising a truncated ellipsoidal reflector open at one end, a rubber diaphragm closing said open end, said reflector having a first focus point within said reflector and a second focus point outside said reflector and beyond said diaphragm, said reflector having an axis of rotation which passes through both of said focus points, said reflector and said diaphragm comprising a volume filled with water, a pair of electrodes in said reflector and having ends in spaced relation providing a spark gap at said first focus point, an electrical spark between said electrodes across said gap producing a shockwave focused by said reflector on said second focus point, the improvement comprising an ultrasound transducer within said reflector and aimed toward said second focus point, and mounting means for said transducer adapted for quick and simple mounting of said transducer, said mounting means comprising a housing open toward said second focus point, said transducer being mounted in said housing, a plurality of arms extending substantially radially from said housing, each arm having an outer end, a plurality of anchor members respectively mounted on said arm outer ends, and a plurality of sockets in said reflector adjacent said open end and respectively receiving said anchor members to mount said transducer substantially at said reflector open end.

2. The lithotripter as set forth in claim 1 wherein each said anchor member comprises a substantially rectangular block.

3. The lithotripter as set forth in claim 2 wherein said blocks and said sockets are precision-formed for a close fit to position said housing accurately.

4. The lithotripter as set forth in claim 1 where at least one of said arms comprises a hollow tube, and wires extending through said tube to said transducer.

5. The lithotripter as set forth in claim 1 wherein said plurality of arms comprises two aligned arms respectively on opposite sides of said housing.

6. The lithotripter as set forth in claim 5 wherein each said anchor member comprises a substantially rectangular block.

7. The lithotripter as set forth in claim 6 wherein said blocks and sockets are precision-formed for a close fit to position said housing accurately.

8. The lithotripter as set forth in claim 7 and further including means for releasably retaining said blocks in said sockets.

9. The lithotripter as set forth in claim 7 wherein said sockets open inwardly of said reflector and at said open end.

10. The lithotripter as set forth in claim 9 wherein said sockets are recessed.

11. The lithotripter as set forth in claim 7 wherein said transducer is mounted on said axis of rotation of said reflector.

12. The lithotripter as set forth in claim 1 wherein each said anchor member has substantially semi-cylindrical opposite ends.

* * * * *